United States Patent
Miyahara et al.

(10) Patent No.: US 10,085,613 B2
(45) Date of Patent: Oct. 2, 2018

(54) ENDOSCOPE

(71) Applicant: OLYMPUS CORPORATION, Tokyo (JP)

(72) Inventors: Hideharu Miyahara, Nagano (JP); Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 41 days.

(21) Appl. No.: 14/919,924

(22) Filed: Oct. 22, 2015

(65) Prior Publication Data
US 2016/0038000 A1    Feb. 11, 2016

Related U.S. Application Data

(63) Continuation of application No. PCT/JP2013/084297, filed on Dec. 20, 2013.

(30) Foreign Application Priority Data

Apr. 26, 2013 (JP) ................... 2013-094286

(51) Int. Cl.
*A61B 1/06* (2006.01)
*A61B 1/00* (2006.01)
(Continued)

(52) U.S. Cl.
CPC .......... *A61B 1/00013* (2013.01); *A61B 1/005* (2013.01); *A61B 1/0017* (2013.01);
(Continued)

(58) Field of Classification Search
CPC ............ A61B 1/00096; A61B 1/00009; A61B 1/00165; A61B 1/00013
(Continued)

(56) References Cited

U.S. PATENT DOCUMENTS 2,975,785 A * 3/1961 Sheldon ............. A61B 1/00165
277/634
4,813,400 A * 3/1989 Washizuka ............... G02B 6/04
385/117

(Continued)

FOREIGN PATENT DOCUMENTS

EP    2626002 A1    8/2013
GB    2341907 A    3/2000
(Continued)

OTHER PUBLICATIONS

International Search Report dated Jan. 21, 2014 issued in PCT/JP2013/084297.
(Continued)

*Primary Examiner* — Matthew J Kasztejna
(74) *Attorney, Agent, or Firm* — Scully, Scott, Murphy & Presser, P.C.

(57) ABSTRACT

An endoscope includes: an insertion portion that includes a distal end portion in which an image sensor and a laser diode are disposed, a bending portion, and a flexible portion, the image sensor outputting an image pickup signal, the laser diode converting the image pickup signal into an optical signal; an operation portion; an universal cord; a connector; an optical fiber that is inserted through the insertion portion and transmits the optical signal; and a stress relief portion that changes an effective length L1 of the optical fiber in accordance with a stress applied to the optical fiber, the effective length being a length of the optical fiber along an insertion direction thereof.

12 Claims, 4 Drawing Sheets

(51) Int. Cl.
  *A61B 1/005* (2006.01)
  *G02B 6/44* (2006.01)
  *A61B 1/05* (2006.01)

(52) U.S. Cl.
  CPC ............ *A61B 1/00126* (2013.01); *A61B 1/05* (2013.01); *G02B 6/444* (2013.01); *A61B 1/00009* (2013.01); *A61B 1/00096* (2013.01); *A61B 1/06* (2013.01)

(58) Field of Classification Search
  USPC .................................................. 600/161, 182
  See application file for complete search history.

(56) References Cited

U.S. PATENT DOCUMENTS

| | | | |
|---|---|---|---|
| 5,275,152 A | 1/1994 | Krauter et al. | |
| 5,443,057 A * | 8/1995 | Elmore | A61B 1/00165 600/133 |
| 5,535,139 A | 7/1996 | Barringer et al. | |
| 5,665,051 A * | 9/1997 | Quick | A61B 1/00165 600/161 |
| 5,894,540 A * | 4/1999 | Drewing | G02B 6/444 385/135 |
| 6,361,360 B1 | 3/2002 | Hwang et al. | |
| 6,478,291 B1 | 11/2002 | Courtney | |
| 6,608,957 B2 * | 8/2003 | Sudo | G02B 6/4471 385/135 |
| 7,857,757 B2 * | 12/2010 | Schaaf | A61B 1/00096 600/182 |
| 8,358,898 B2 * | 1/2013 | Ayme | B65H 75/4476 385/135 |
| 8,463,439 B2 * | 6/2013 | Blumenkranz | A61B 34/30 385/33 |
| 8,622,481 B2 * | 1/2014 | Niederriter | E21C 29/14 299/43 |
| 2004/0158159 A1 | 8/2004 | Seto et al. | |
| 2010/0250000 A1 | 9/2010 | Blumenkranz et al. | |
| 2011/0034769 A1 | 2/2011 | Adair et al. | |
| 2013/0096380 A1 | 4/2013 | Matsuzawa et al. | |

FOREIGN PATENT DOCUMENTS

| | | |
|---|---|---|
| JP | S62-275425 A | 11/1987 |
| JP | H05-184039 A | 7/1993 |
| JP | H06-269401 A | 9/1994 |
| JP | H10-127570 A | 5/1998 |
| JP | 2001-082986 A | 3/2001 |
| JP | 2002-526017 A | 8/2002 |
| JP | 2004-229742 A | 8/2004 |
| JP | 2004-273606 A | 9/2004 |
| JP | 2007-260066 A | 10/2007 |
| JP | 2012-170742 A | 9/2012 |
| JP | 5155496 B2 | 3/2013 |
| TW | 525326 B | 3/2003 |
| WO | WO 00/17980 A1 | 3/2000 |
| WO | WO 2012/046856 A1 | 4/2012 |

OTHER PUBLICATIONS

Partial translation of JP H07-032758 B2, dated Apr. 12, 1995.
Extended Supplementary European Search Report dated Dec. 2, 2016 in related European Patent Application No. 13 88 3326.4.

* cited by examiner

FIG. 2
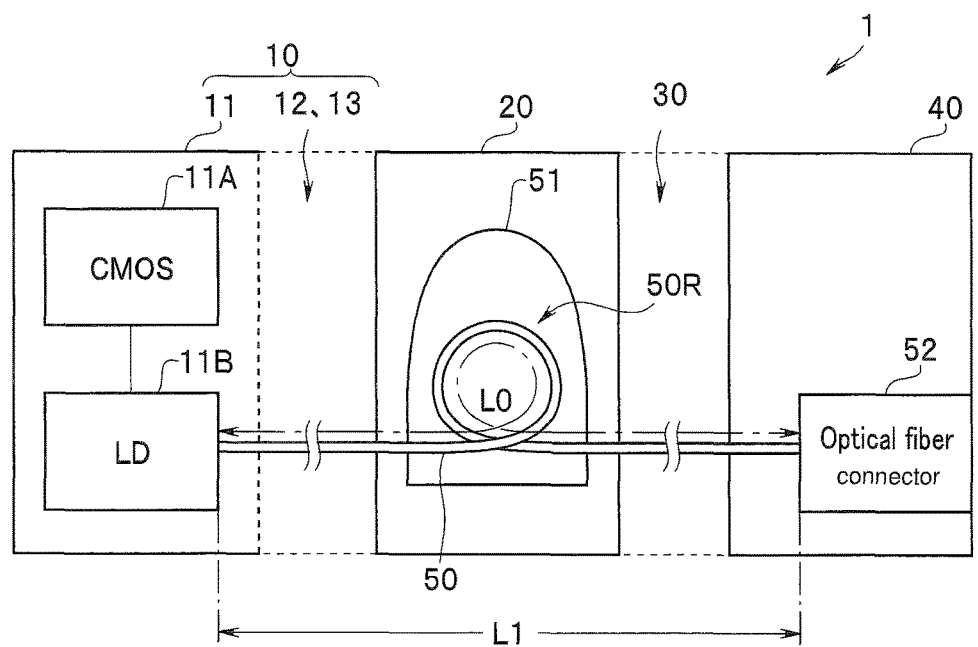
FIG. 3A  FIG. 3B  FIG. 3C
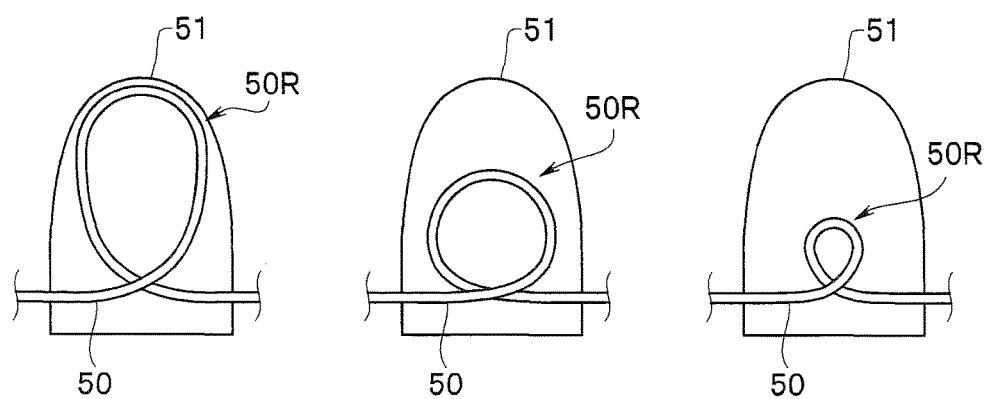

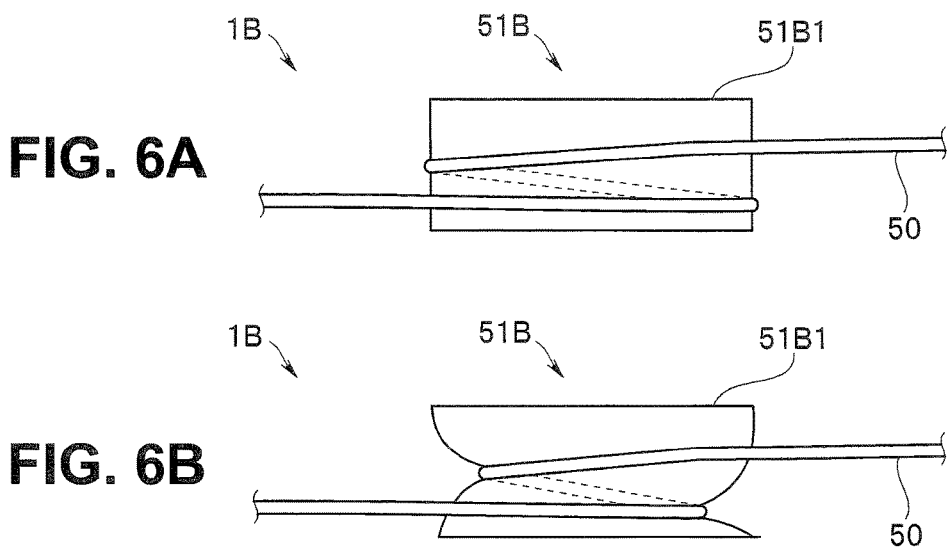
FIG. 6A
FIG. 6B
FIG. 7
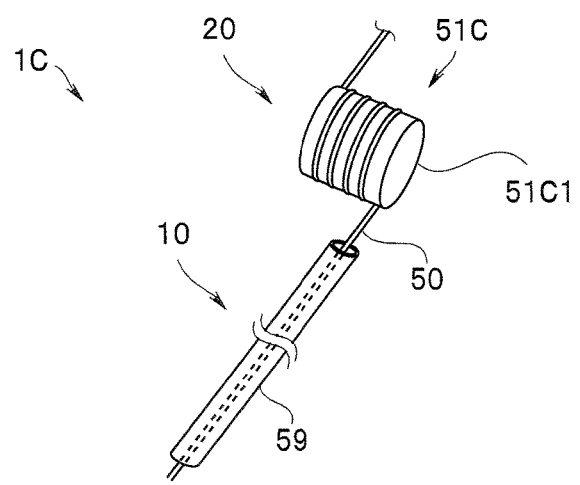

//<br>

ENDOSCOPE

CROSS REFERENCE TO RELATED APPLICATION

This application is a continuation application of PCT/JP2013/084297 filed on Dec. 20, 2013 and claims benefit of Japanese Application No. 2013-094286 filed in Japan on Apr. 26, 2013, the entire contents of which are incorporated herein by this reference.

BACKGROUND OF INVENTION

1. Field of the Invention

The present invention relates to an endoscope in which an image pickup signal is transmitted through an optical fiber.

2. Description of the Related Art

An endoscope makes it possible to observe the inside that cannot be observed from outside, by an endoscopic image, with an insertion portion being inserted into a deep part through a thin gap or the like.

In order to make more certain judgment, an endoscopic image of higher image quality has been required. Since an image signal of the endoscopic image of high image quality includes a large amount of capacity, an endoscope in which transmission is performed through an optical fiber instead of a conventional metal cable is disclosed in Japanese Patent Laid-Open Publication No. 2007-260066.

SUMMARY OF THE INVENTION

An endoscope according to an embodiment of the present invention includes: an insertion portion that comprises a distal end portion in which an image pickup section and a light emitting device section are disposed, a bending portion for changing a direction of the distal end portion, and a flexible portion having flexibility and extended from the bending portion, the image pickup section outputting an image pickup signal, the light emitting device section converting the image pickup signal into an optical signal; an operation portion that is disposed on a proximal end side of the insertion portion; an universal cord that is extended from the operation portion; a connector that is disposed on a proximal end side of the universal cord; an optical fiber that is inserted through the insertion portion and transmits the optical signal; and a stress relief portion that changes an effective length of the optical fiber in accordance with a stress applied to the optical fiber, the effective length being a length of the optical fiber along an insertion direction thereof.

BRIEF DESCRIPTION OF THE DRAWINGS

FIG. 2 is a configuration diagram for explaining an optical fiber route of the endoscope according to a first embodiment;

FIG. 3A is a side view for explaining a function of a stress relief portion of the endoscope according to the first embodiment;

FIG. 3B is a side view for explaining the function of the stress relief portion of the endoscope according to the first embodiment;

FIG. 3C is a side view for explaining the function of the stress relief portion of the endoscope according to the first embodiment;

FIG. 6A is a side view for explaining structure of a stress relief portion of an endoscope according to a third embodiment;

FIG. 6B is a side view for explaining the structure of the stress relief portion of the endo scope according to the third embodiment; and FIG. 7 is a perspective view for explaining an optical fiber route and so forth in an endoscope according to a fourth embodiment.

DETAILED DESCRIPTION OF THE PREFERRED EMBODIMENT(S)

First Embodiment

Figure 1:
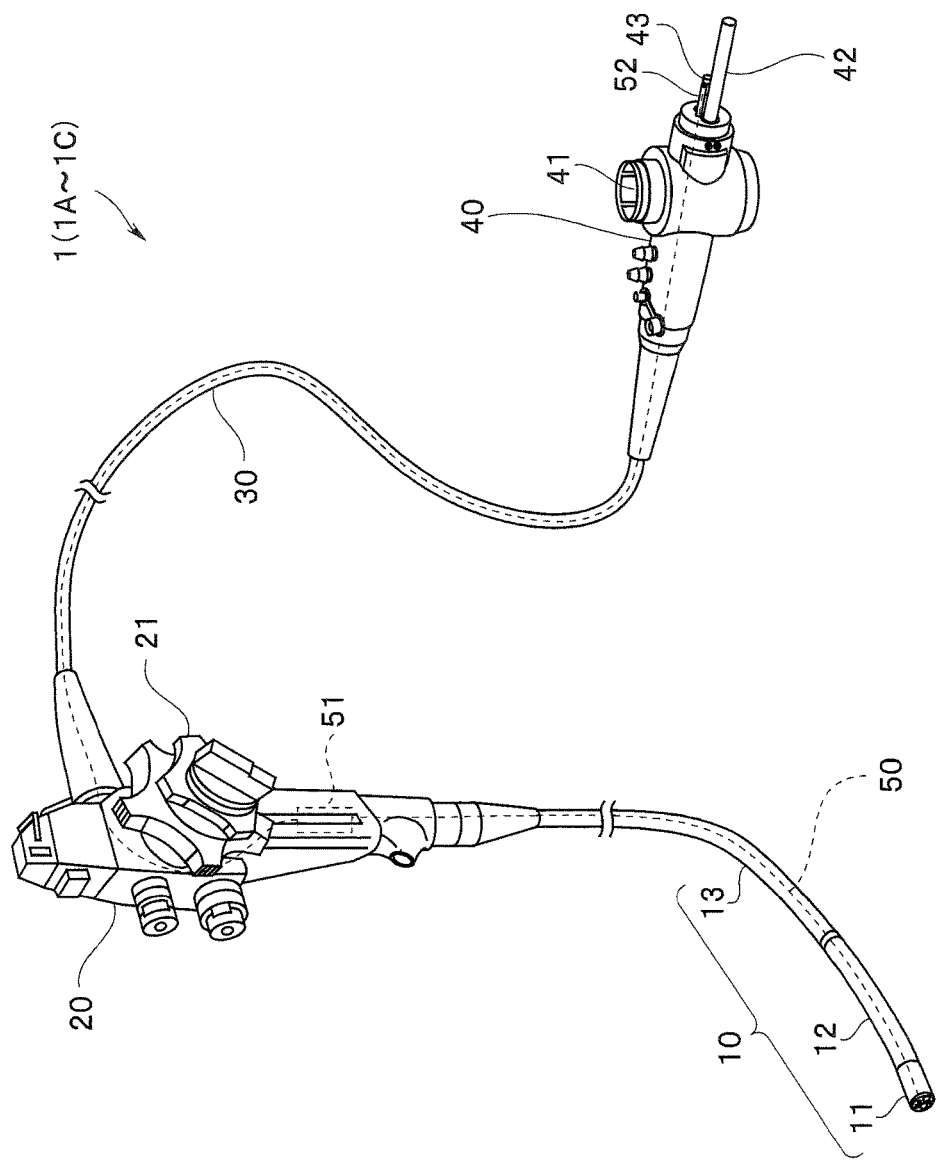
FIG. 1 is a perspective view of an endoscope in embodiments.

As shown in FIG. 1, an endoscope 1 of the present embodiment is provided with an insertion portion 10, an operation portion 20 disposed on a proximal end side of the insertion portion 10, a universal cord 30 provided to extend from the operation portion 20 and a connector 40 disposed on a proximal end side of the universal cord 30.

The insertion portion 10 is comprised of a distal end portion 11, a bending portion 12 for changing a direction of the distal end portion 11, and a flexible portion 13 having flexibility and provided to extend from the bending portion 12. At the operation portion 20, an angle knob 21 for operating the bending portion 12 is disposed and a stress relief portion 51, as described later, is disposed. The connector 40 for connection with a processor (not shown) includes an electric connector portion 41, a light guide connecting portion 42, an air feeding pipe 43 and an optical fiber connector 52. Further, in the endoscope 1, an optical fiber 50 which transmits an optical signal is inserted through from the distal end portion 11 to the connector 40 via the stress relief portion 51.

As shown in FIG. 2, an image sensor 11A as an image pickup section which outputs an image pickup signal, and a laser diode (LD) 11B as a light emitting device section which converts the image pickup signal into the optical signal are disposed in the distal end portion 11 of the endoscope 1. As the image sensor 11A, a CMOS (Complementary Metal Oxide Semiconductor) image sensor is used, but a CCD (Charged Coupled Device) may be used. Besides, in a case where the image pickup signal outputted from the image sensor 11A is an analog signal, the analog signal is converted into a digital signal by an A/D converter, which is not shown, and is further converted into a LD drive signal for blinking the LD 11B, by a LD driver which is not shown.

In the endoscope 1, the image pickup signal is converted into the optical signal by the LD 11B and transmitted to the connector 40 through the optical fiber 50. Then, the optical signal is converted into an electric signal again by a light receiving section of the processor (not shown) connected with the connector 40, and is processed to be an endoscopic image signal for displaying on a display section.

As already described, in the endoscope 1 in which the signal is transmitted by the optical fiber 50, in accordance with deformation of the bending portion, the insertion portion having flexibility or the universal cord having flexibility, a stress is applied to the optical fiber 50 which is inserted through these elements.

The stress relief portion 51 is disposed at the operation portion 20 in the middle of a route of the optical fiber 50 of the endoscope 1. The stress relief portion 51 changes an effective length L1 of the optical fiber 50 in accordance with a stress applied to the optical fiber 50, to thereby reduce the stress. In the present specification, the effective length L1 means a length of the optical fiber 50 along an insertion direction.

As shown in FIG. 2, the optical fiber 50 includes a winding portion (a loop portion) 50R formed by a winding of one turn in the stress relief portion 51. That is, the effective length L1 is shorter than an actual length L0 of the optical fiber 50.

As shown in FIGS. 3A-3C, a size of the winding portion 50R and thus the effective length L1 change in accordance with the stress applied to the optical fiber 50. Since the optical fiber 50 has rigidity, when a compression stress is applied and the winding portion 50R is large (FIG. 3A), the effective length L1 is short, and when a tensile stress is applied and the winding portion 50R is small (FIG. 3C), the effective length L1 becomes long.

Since the applied stress is reduced at the stress relief portion 51, in the endoscope 1 there is a little fear that the optical fiber 50 is damaged or broken and thus is excellent in durability.

It is noted that the stress relief portion 51 may be the operation portion 20 itself in which the winding portion 50R is arranged inside. However, in order to prevent damages of the optical fiber 50 effectively, it is preferable that the stress relief portion 51 is a dedicated protection case in which the optical fiber 50 is housed such that the winding portion 50R does not come in contact with other members when the winding portion 50R deforms. It is preferable that at least a part of an internal shape of the protection case is composed of a curved line to correspond with a shape of the winding portion 50R, as shown in FIG. 2, etc.

It is noted that a stress reduction effect is obtained when the number of turns of the winding portion 50R is at least one turn. When the number of turns is large, a difference ΔL between the actual length L0 and the effective length L1 becomes large. The difference ΔL is preferably not less than 1% and not more than 10% of L0. When the difference ΔL is not less than the above ratio, the stress reduction effect is remarkable. When the difference ΔL exceeds the above range, a loss in optical transmission becomes large. The difference ΔL exceeds 10% when the number of turns exceeds 20 turns, for example.

Besides, it may be configured that the stress relief portion 51 is disposed in an insertion route of the optical fiber 50, and for example, the stress relief portion 51 may be disposed in the connector 40. Further, a plurality of stress relief portions 51 may be disposed along the insertion route of the optical fiber 50.

Further, it may be configured such that the optical fiber 50 is inserted through from the distal end portion 11 to the operation portion, and a light receiving section for converting the optical signal to the electric signal is disposed at the operation portion 20. In this case, it is preferable that the stress relief portion 51 is disposed at the operation portion 20 at a proximal end side of the insertion route of the optical fiber 50.

Second Embodiment

An endoscope 1A according to a second embodiment is similar to the endoscope 1, and therefore the same reference signs are assigned to the elements having the same functions and the description thereof is omitted.

Figure 4:
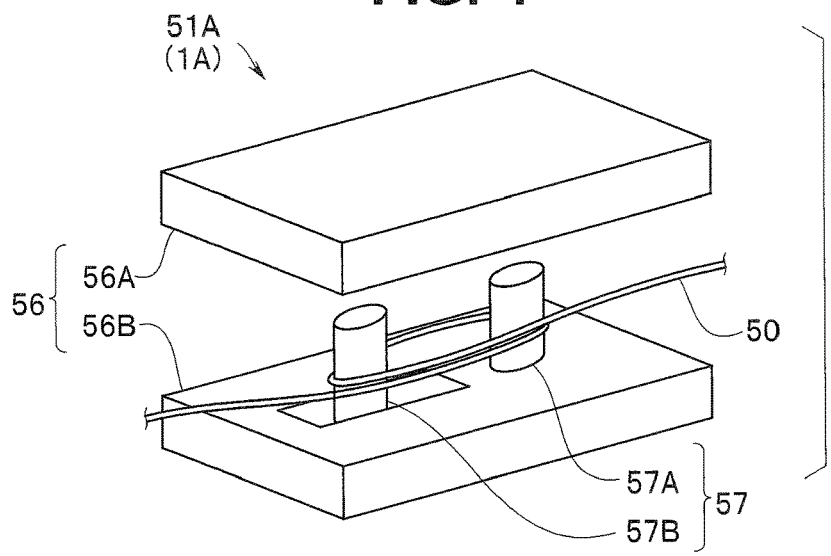
FIG. 4 is a perspective exploded view for explaining structure of a stress relief portion of an endoscope according to a second embodiment.
Figure 5A:
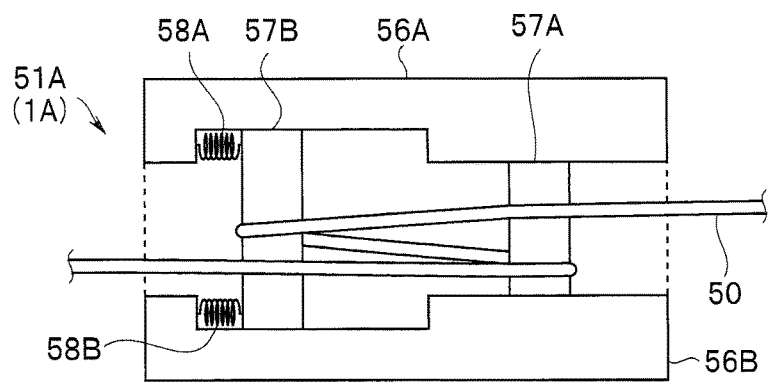
FIG. 5A is a side view for explaining the structure of the stress relief portion of the endo scope according to the second embodiment.
Figure 5B:
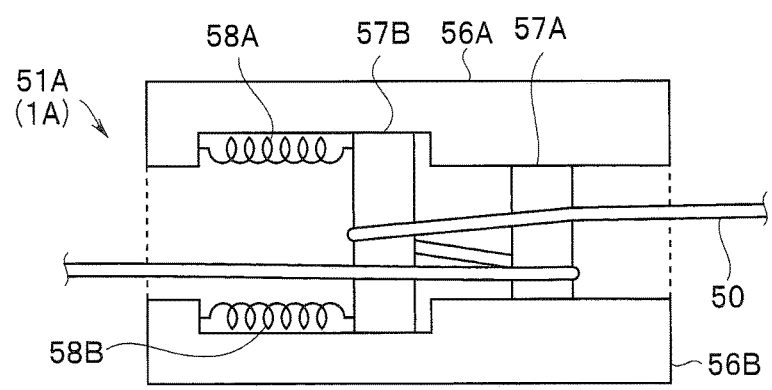
FIG. 5B is a side view for explaining the structure of the stress relief portion of the endo scope according to the second embodiment.

As shown in FIGS. 4, 5A and 5B, a stress relief portion 51A of the endoscope 1A according to the present embodiment includes two columns 57A and 57B around which the optical fiber 50 is wound, and which is configured such that a distance between the columns changes in accordance with a stress applied to the optical fiber 50.

As shown in FIGS. 5A and 5B, the column 57A is fixed to support plates 56 (56A, 56B), but the column 57B is configured to be movable in a direction toward the column 57A.

When no tensile stress is applied to the optical fiber 50, the distance between the two columns 57A and 57B is long by actions of springs 58A and 58B, as shown in FIG. 5A. In contrast, when a tensile stress is applied to the optical fiber 50, the distance between the two columns 57A and 57B becomes short, as shown in FIG. 5B. When the distance between the two columns 57A and 57B becomes short, the effective length L1 of the optical fiber 50 becomes long, so that the stress is relieved.

The endoscope 1A has the advantageous effects of the endoscope 1 and the stress relief portion is small in size, and since the optical fiber 50 is held in a stable form by biasing forces of the springs 58A and 58B, the endoscope 1A is further excellent in durability.

Besides, the two columns 57 may be semispherical cylinders or elliptical cylinders, for example, as long as a surface in contact with the optical fiber 50 is comprised of a curved surface, and a groove corresponding to a diameter of the optical fiber 50 may be formed.

Third Embodiment

An endoscope 1B according to a third embodiment is similar to the endoscopes 1, 1A, and therefore the same reference signs are assigned to the elements having the same functions and the description thereof is omitted.

As shown in FIGS. 6A and 6B, a stress relief portion 51B of the endoscope 1B according to the present embodiment includes an elastic member 51B1 around which the optical fiber 50 is wound.

As shown in FIG. 6B, the elastic member 51B1 made of a silicone rubber, a sponge material or the like in a cylindrical shape, for example, is deformed by a tensile stress applied to the optical fiber 50 so that a diameter is decreased, and therefore the effective length L1 of the optical fiber 50 becomes long so that the stress is relieved. It is preferable that the elastic member 51B1 has a contact surface in contact with the optical fiber 50 that is composed of a curved surface. Further, a leaf spring in a circular shape which has a function of an elastic member, or the like may be used.

The endoscope 1B has the advantageous effects of the endoscope 1A and is further simple in structure.

Fourth Embodiment

An endoscope 1C according to a fourth embodiment is similar to the endoscopes 1, 1A, 1B, and therefore the same reference signs are assigned to the elements having the same functions and the description thereof is omitted.

As shown in FIG. 7, a stress relief portion 51C of the endoscope 1C according to the present embodiment includes an elastic member 51C1 around which the optical fiber 50 is wound a plurality of times.

Further, in the endoscope 1C, the optical fiber 50 is inserted through a sheath pipe 59 in the insertion portion 10.

If the optical fiber 50 comes in contact with other members in the insertion portion 10, there is a fear that the optical fiber 50 is damaged. However, in the endoscope 1C, since the optical fiber 50 is inserted through the sheath pipe 59, there is no fear of coming in contact with other members.

That is, the sheath pipe 59 has an inner diameter which is 1.5 to 5 times larger than a diameter of the optical fiber 50 and the optical fiber 50 inserted through the sheath pipe 59 is movable forward and backward easily. For example, a friction coefficient of an inner wall of the sheath pipe 59 which is made of fluororesin, for example, is small and there is no fear of causing damage on the optical fiber 50 when the optical fiber moves. Therefore, the endoscope 1C has the advantageous effects of the endoscope 1B, etc. and further is excellent in durability.

Besides, in a case where the optical fiber 50 is inserted through the universal cable 30, it is preferable to dispose the sheath pipe 59 in the universal cable 30. Further, the sheath pipe 59 may be divided into a plurality of pieces in the insertion portion 10 and may be not disposed over the entire length of the insertion portion 10.

The present invention is not limited to the above-described embodiments, etc. and may be subjected to various changes, modifications, combinations and the like within a range in which the gist of the present invention is not changed.

What is claimed is:

1. An endoscope comprising:
   an insertion portion that comprises a distal end portion in which an image pickup section and a light emitting device section are disposed, a bending portion for changing a direction of the distal end portion, and a flexible portion having flexibility and extended from the bending portion, the image pickup section outputting an image pickup signal, the light emitting device section converting the image pickup signal into an optical signal;
   an operation portion that is disposed on a proximal end side of the insertion portion;
   an universal cord that is extended from the operation portion;
   a connector that is disposed on a proximal end side of the universal cord;
   an optical fiber that is inserted through the insertion portion and transmits the optical signal; and
   a stress relief portion that changes an effective length of the optical fiber in accordance with a stress applied to the optical fiber, the effective length being a length of the optical fiber along an insertion direction thereof;
   wherein the stress relief portion includes an elastic member wound with the optical fiber such that the stress applied to the optical fiber deforms the elastic member to change the effective length of the optical fiber; and
   the optical fiber is wound by at least one complete turn around the elastic member.

2. The endoscope according to claim 1, wherein the stress relief portion is disposed at the operation portion.

3. The endoscope according to claim 2, wherein the stress relief portion includes two columns around which the optical fiber is wound, and a distance between which changes in accordance with the stress applied to the optical fiber.

4. The endoscope according to claim 2, wherein at least a part of the stress relief portion has a curved line to correspond with a shape of a winding portion where the optical fiber is wound, and the stress relief portion is a protection case in which the optical fiber is housed such that the winding portion does not come in contact with other members when the winding portion deforms.

5. The endoscope according to claim 1, wherein the optical fiber is inserted through a sheath pipe in the insertion portion.

6. The endoscope according to claim 1, wherein the elastic member has a cylindrical shape.

7. The endoscope according to claim 1, wherein the elastic member is formed of one of a silicone rubber or a sponge material.

8. The endoscope according to claim 1, wherein the elastic member has a contact surface in contact with the optical fiber, the contact surface being a curved surface.

9. The endoscope according to claim 1, wherein the elastic member is deformed by a tensile stress applied to the optical fiber so that a diameter of the elastic member is decreased to increase an effective length of the optical fiber to relieve stress in the optical fiber.

10. An endoscope comprising:
    an insertion portion including a bending portion for changing a direction of a distal end portion;
    an operation portion disposed on a proximal end side of the insertion portion;
    an optical fiber that is inserted through the insertion portion and operation portion; and
    an elastic member arranged in the operation portion, the elastic member changing an effective length of the optical fiber in accordance with a stress applied to the optical fiber, the effective length being a length of the optical fiber along an insertion direction thereof;
    wherein the elastic member is wound with the optical fiber such that the stress applied to the optical fiber deforms the elastic member to change the effective length of the optical fiber; and
    the optical fiber is wound by at least one complete turn around the elastic member.

11. The endoscope according to claim 1, wherein the stress relief portion changes the effective length of the optical fiber by changing a length of the optical fiber which contacts the elastic member.

12. The endoscope according to claim 10, wherein the stress relief portion changes the effective length of the optical fiber by changing a length of the optical fiber which contacts the elastic member.

* * * * *